United States Patent [19]

Sumida et al.

[11] Patent Number: 4,709,057

[45] Date of Patent: Nov. 24, 1987

[54] METHOD OF PREPARING FINE CRYSTAL PARTICLES OF MALEIC ANHYDRIDE

[75] Inventors: Seizi Sumida; Kaichi Ono; Kazuo Yoshida, all of Oita; Tomozo Yamada, Tokyo, all of Japan

[73] Assignee: Nippon Oil and Fats Co., Ltd., Tokyo, Japan

[21] Appl. No.: 903,230

[22] Filed: Sep. 3, 1986

[30] Foreign Application Priority Data

Sep. 10, 1985 [JP] Japan .................................. 60-198538
Sep. 28, 1985 [JP] Japan .................................. 60-213649

[51] Int. Cl.$^4$ .......................................... C07D 307/60
[52] U.S. Cl. ...................................... 549/262; 260/707
[58] Field of Search ................. 549/262, 247; 260/707

[56] References Cited

PUBLICATIONS

Jansons et al., Latvian P S R Zinat. Akad. Vestis, Kim. Ser., vol. 1, pp. 116–117, (1971); Chem. Ab., 75, 26211t (1975).

Primary Examiner—Richard A. Schwartz
Assistant Examiner—Bernard I. Dentz
Attorney, Agent, or Firm—Majestic, Gallagher, Parsons & Siebert

[57] ABSTRACT

A method of preparing fine crystal particles of maleic anhydride is provided. The method contains the steps of putting a molten mass of maleic anhydride into a hermetically closed container moved at a moving rate of 1 to 30 times per minute and cooling the molten mass to room temperature over three hours or more. A maleic anhydride composition contains 0.01 to 5 wt. parts of colloidal silica relative to 100 wt. parts of maleic anhydride particles.

6 Claims, No Drawings

METHOD OF PREPARING FINE CRYSTAL PARTICLES OF MALEIC ANHYDRIDE

BACKGROUND OF THE INVENTION

1. Field of the Invention

The present invention relates to a method of preparing fine crystal particles of maleic anhydride, and to a maleic anhydride composition containing such fine crystal particles of maleic anhydride.

2. Related Art Statement

Maleic anhydride has been used for modifying various properties of polyolefins, including adhesiveness, dyeing properties or dyeabilities and plating properties of such resins. In the conventional process wherein a molten mass of maleic anhydride is cooled spontaneously under stationary condition, the entire molten mass is solidified and crystallized to form a large plate-shaped or lumps of crystals. However, there is a demand for maleic anhydride of fine particle form, since the fine particles are more easily handled and is improved in dispersibility and operation efficiency.

The known methods for preparing maleic anhydride of fine particle form include recrystallization of maleic anhydride from a solution in an organic solvent, such as acetone, toluene or benzene, and mechanical pulverization effected by using a feather mill (a knife hammer rotation type of screen mill) which pulverizes maleic anhydride blocks by shearing action.

Although crystals of maleic anhydride in fine particle form may be prepared by dissolving a raw maleic anhydride material in a solvent to form a solution from which maleic anhydride is recrystallized, the yield of the product is relatively low. Further disadvantages of the recrystallization method are that it involves additional steps of removing the solvent from the fine particles of maleic anhydride and recovering the solvent, and that the use of a solvent poses problems of danger and pollution of environment. Furthermore, a trace of water contained in the organic solvent used readily reacts with maleic anhydride to thereby increase the content of free maleic acid in the product.

On the other hand, when maleic anhydride having a low melting point (52.5° C.) which is one of the materials sensitive to heat is pulverized through a mechanical pulverization method, it is necessary to decrease heat to be generated at pulverization step and to remove the generated heat as soon as possible. For this reason, it becomes necessary to obviate the use of pulverization mechanism which generates a large amount of heat and to provide means for remove the generated heat. As a result, a relatively expensive pulverization equipment is needed to thus cause an economical problem.

Alternatively, maleic anhydride of fine particle form readily cakes so that caking of maleic anhydride particles occurs only by storing the same for several hours. Due to caking of fine maleic anhydride particles occurred during storage and transportation thereof, the fine maleic anhydride particles prepared by the conventional method must be crushed by a wooden hammer or similar tools to separate particles before use. In order to improve operation efficiency at weighing and mixing steps, there is a demand for maleic anhydride which is kept in the form of fine particle to thus have good fluidity so that it can be used without the occurrence of disadvantageous caking phenomenon.

OBJECTS AND SUMMMARY OF THE INVENTION

Accordingly, a principal object of this invention is to provide a method of preparing fine crystal particles of maleic anhydride having high quality at high yield and to provide a maleic anhydride composition containing such fine particles of maleic anhydride.

Another object of this invention is to provide a method of preparing fine crystal particles of maleic anhydride through a simple process without using a solvent and to provide a maleic anhydride composition containing such fine crystal particles of maleic anhydride.

A further object of this invention is to provide a method of preparing fine crystal particles of maleic anhydride having high purity, which is low in content of free maleic acid, and to provide a maleic anhydride composition containing such fine crystal particles of maleic anhydride.

A still further object of this invention is to provide a method of preparing fine crystal particles of maleic anhydride, which is excellent in heat resistant property, and to provide a maleic anhydride composition containing such fine crystal particles of maleic anhydride.

A further object of this invention is to provide a method of preparing fine crystal particles of maleic anhydride having uniform particle size, which is particularly suitable for the modification of polyolefins and to provide a maleic anhydride composition containing such fine crystal particles of maleic anhydride.

A further object of this invention is to provide a maleic anhydride composition containing fine crystal particles of maleic anhydride, which is excellent in fluidity so as to be easily handled without causing caking phenomenon.

The above and other objects of this invention will become apparent from the following description.

A method of preparing fine crystal particles of maleic anhydride, provided in accordance with this invention, comprises the steps of putting a molten mass of maleic anhydride into a hermetically closed container moved at a moving rate of 1 to 30 times per minute, and slowly cooling the molten mass of maleic anhydride to room temperature over a period of not less than 3 hours while keeping separated cryatals of maleic anhydride under the moving condition.

Also included in this invention is a maleic anhydride composition of fine particle form comprising 100 parts by weight of fine crystal particles of maleic anhydride and 0.01 to 5 parts by weight of colloidal silica.

DESCRIPTION OF THE INVENTION

The present invention will now be described in detail hereinbelow.

A method of preparing fine crystal particles of maleic anhydride, according to this invention, will be initially described.

The starting maleic anhydride material used in the method of this invention is any of the purified maleic anhydride products produced through the conventional processes. At a first step of the method of this invention, maleic anhydride may be melted to form a molten mass of maleic anhydride. Alternatively, a molten mass of maleic anhydride may preferably be transferred directly from the final step of a process for preparing maleic anhydride. The starting maleic anhydride is heated to a temperature higher than the melting point, i.e. 52.5° C., of maleic anhydride, and the molten mass is preferably melted and maintained at a temperature within a temperature range of from about 55° to 100° C. although the melting temperature is not critical.

The molten mass of maleic anhydride is then put into a hermetically closed container which is moved continuously or periodically. The moving container used in the method of this invention for containing therein the molten mass of maleic anhydride is sealed or hermetically closed to prevent the content therein from leaking out of the container. Specific examples of the container which may be used conveniently in the method of this invention are cylindrical or box-shaped containers made of stainless steel or other metals, and bags made of a synthetic resin such as polyethylene. The container is moved at a moving rate ranging from 1 to 30 times per minute, preferably from 5 to 20 times per minute, for example by rotating or swinging it continuously or inverting it periodically or intermittently. One side edge of the container may be pivoted and the opposed side edge thereof may be moved in the vertical direction to keep the container and the content therein under continuously moving condition. If the moving rate of the container is less than one time per minute, the content therein is not stirred sufficiently for preventing formation of large plate-shaped blocks of separated crystals. On the contrary, if the container is moved at a moving rate of more than 30 times per minute, large blocks of separated crystals are formed at the vicinity of the container wall, for example, due to centrifugal force when the movement of the container is effected by continuous rotation. The moving rate of the container is counted such that one revolution of the container corresponds to one time movement when it is moved by continouous rotation, and one reciprocal cycle of the container corresponds to one time movement when it is moved by periodic invertion or swinging operation.

According to an important aspect of this invention, the separated crystals are moved in the container until the entire mass of maleic anhydride is cooled to room temperature at a slow cooling rate so that the fine particles of crystals being separated are prevented from adhering to the wall of the container or coagulating to form large lumps or blocks. As the liquid molten mass of maleic anhydride is cooled slowly while the mass is kept moving continuously and gently, fine crystal particles are separated so that the cooled mass becomes a paste containing some part of the thus separated crystal particles and the remaining part of molten liquid maleic anhydride. The viscosity of the pasty mixture composed of the crystallized and liquid phases is gradually increased as the proportion of the crystallized phase is increased with the lapse of time. According to an advantageous merit of the slow cooling with gentle movement of the molten mass at a cooling rate and at a moving rate as defined in the claims, the entire mass of the molten maleic anhydride is uniformly cooled while formation of a large single crystal is prevented. Although the fine crystal particles at the initial stage of separation from the molten liquid phase are heated to higher temperature due to latent heat of solidification, they are cooled by the liquid phase since they are kept moving through the liquid mass during the cooling step. As a result, the temperature of entire system including the crystallized solid phase and the molten liquid phase of maleic anhydride is lowered evenly throughout the cooling step to thereby provide the advantageous effect that the maleic anhydride product prepared through the method of this invention is kept in a fine particle or minute grain form until it reaches room temperature.

According to this invention, it has been found that the molten mass of maleic anhydride should be slowly cooled to room temperature, while being kept moving, over a period of not less than 3 hours, preferably from 5 to 24 hours. Cooling may proceed spontaneously, or by forced cooling if necessary. If the molten mass is cooled at an excessively higher rate such that the entire mass is cooled to room temperature within a period of less than 3 hours, undesirable rapid coagulating of crystals takes place to result in formation of large plate-shaped blocks or to result in formation of a single large block in the extreme case.

Crystal grains or particles obtained by the method of this invention pass through a 10 mesh sieve, preferably pass through 28 mesh sieve, and more preferably pass through a 28 to 115 mesh sieve.

The method of this invention provides high quality fine crystals of maleic anhydride at high yield through a simplified process as compared with the conventional processes.

According to a further aspect of this invention, the crystals of maleic anhydride in fine particle form may be mixed with colloidal silica to provide a maleic anhydride composition by mixing 100 parts by weight of the product of this invention with 0.01 to 5 parts by weight, preferably from 0.1 to 0.5 parts by weight, of colloidal silica. If the mixed amount of colloidal silica is less than 0.01 part by weight, caking may occur at some portion of the composition to thus result in failure for the improvement of fluidity. It is difficult to form a uniform mixture containing more than 5 parts by weight of colloidal silica mixed with 100 parts by weight of the crystals of maleic anhydride in particle form, since colloidal silica is relatively light (Specific Gravity: 50 gl) and has the tendency of scattering or floating. In addition, the transparency of a modified polyolefin is adversely affected if a maleic anhydride composition containing more than 5 parts of colloidal silica, per 100 parts by weight of the crystals of maleic anhydride, is used for the purpose of modification of the polyolefin.

A colloidal silica powder may be mixed with the maleic anhydride particles, prepared in accordance with the invention, in a tumbler type mixer. Otherwise, a desired quantity of colloidal silica may be added to the molten mass of maleic anhydride, followed by cooling to crystallize maleic anhydride as described hereinbefore. Either of hydrophilic or hydrophobic colloidal silica may be used to exhibit the advantageous function of preventing the blocking phenomenon.

When a colloidal silica powder is mixed with the maleic anhydride particles of this invention, a suitable material may be selected from various commercial products having particle sizes ranging from 5 to 50 microns. When a colloidal silica powder is added to the molten mass of maleic anhydride prior to the cooling step, it is preferred to use hydrophobic colloidal silica since the grain size of each separated maleic anhydride crystal tends to become larger if hydrophilic colloidal silica is used.

By the addition of a small quantity of colloidal silica to the maleic anhydride particles of this invention, a maleic anhydride composition excellent in fluidity and without causing caking problem may be prepared. The maleic anhydride composition, thus provided by this invention, may be handled easily and may be used as a material for modifying polyolefins without deteriorating the transparency, adhesiveness and other properties of the modified resin.

EXAMPLES OF THE INVENTION

The present invention will be described more specifically with reference to some examples thereof and comparative examples.

EXAMPLE 1

Into a stainless steel container having a charge volume of 120 liters (Length: 100 cm, Width: 60 cm, Height: 20 cm), put was 50 kg of liquid maleic anhydride which had been deliverd from a distillation step from the process for the production of maleic anhydride and maintained at 70° C. After closing the container, the content therein was cooled spontaneously to the room temperature over a period of 10 hours, while rotating the container at a rate of 5 rpm, to separate fine crystal particles. The thus formed crystal particles were sieved through a 10 mesh metal screen to obtain 48.5 kg (Yield: 97%) of crystals of maleic anhydride of fine particle form having a particle size of passing through 10 mesh screen. The properties of the particle-form crytal product are shown in Table 1.

EXAMPLE 2

The procedure as described in Example 1 was repeated except that the container was rotated at a rate of 10 rpm and that the cooling rate was further lowered such that the entire mass had been cooled to the room temperature over a period of 15 hours, whereby 48.2 kg (Yield: 96%) of crystals of maleic anhydride of fine particle form was prepared.

EXAMPLE 3

10 kg of molten maleic anhydride maintained at 60° C. was put into a 20 liter polyethylene bag which was closed by heat sealing. One side edge of the bag was swingably pivoted and the opposed side edge of the bag was connected to a rotary motor fitted with a reduction gear to be movable in the vertical direaction at a rate of 20 times per minute. The content in the container was cooled spontaneously for 5 hours until it reached the room temperature while being moved continuously, whereupon fine crystal particles were separated. The following procedures were the same as described in Example 1 to obtain 9.8 kg (Yield: 98%) of a final product of fine crystal particle form.

COMPARATIVE EXAMPLE 1

Into a 300 liter stainless steel reaction vessel, charged were 50 liters of acetone and 200 kg of tablet-shaped maleic anhydride, and then the mixture in the vessel was heated under agitation at 50° to 55° C. to dissolve maleic anhydride in acetone. Thereafter, the content in the vessel was cooled to 25° C. by passing cooling water through the jacket of the reaction vessel to recrystallize maleic anhydride. After filtering, the separated fine crystal particles were put into a reduced pressure drier, and acetone was evaporated off at a temperature of 25° to 35° C. to obtain 90 kg (Yield: 45%) of a final product of fine crystal particle form. The properties of the thus formed final product are shown in Table 1.

COMPARATIVE EXAMPLE 2

Generally following the procedures as set forth in Example 1, except that the rate of rotation of the container was changed to 50 rpm. The result was that large plate-shaped blocks were formed along the walls of the container, and only 24 kg (Yield: 48%) of crystals of maleic anhydride of fine particle form was left in the container.

COMPARATIVE EXAMPLE 3

Generally following the procedures as set forth in Example 1, except that the cooling time was changed to 2 hours. The result was that large plate-shaped blocks were formed, and only 28 kg (Yield: 46%) of crystals of maleic anhydride of fine particle form was left in the container.

TABLE 1

|  | Example 1 | Comparative Example 1 |
|---|---|---|
| Analytical Test |  |  |
| Color of Molten Mass (APHA)*[1] | 10 | 10 |
| Solidifying Point (°C.) | 52.7 | 52.4 |
| Content of Maleic Acid (%) | 0.09 | 0.65 |
| Content of Maleic Anhydride (%) | 99.9 | 99.3 |
| Resistance to Heating (APHA)*[2] (Color of Molten Mass after 180° C. × 2 Hr) | 60 | 150 |
| Yield (%) | 97 | 45 |
| Particle Size Distribution |  |  |
| 10 to 20 meshes (wt %) | 3 | 1 |
| 20 to 28 meshes (wt %) | 3 | 1 |
| 28 to 42 meshes (wt %) | 60 | 50 |
| 42 to 60 meshes (wt %) | 20 | 20 |
| 60 to 80 meshes (wt %) | 5 | 10 |
| 80 to 100 meshes (wt %) | 5 | 10 |
| 100 to 115 meshes (wt %) | 4 | 5 |
| 115 to 150 meshes (wt %) | 0 | 3 |

Amongst the results shown in Table 1, the Color of Molten Mass (APHA)*[1] was determined by the following test method as stipulated in JIS K 4101. A test sample was put into a transparent and colorless test tube provided with ground glass plug and having an inner diameter of 25 cm and a length of 16 cm. The sample in the test tube was melted at 65° C., and color of the molten mass in the test tube was compared with those of the standard color series to determine the corresponding color of the molten sample mass.
The Resistance to Heating (APHA)*[2] set forth in Table 1 was determined by the following test method. The test tube containing the molten maleic anhydride sample, as described in the preceding paragraph, was dipped in an oil bath maintained at 180° C. for 60 minutes, and then removed from the oil bath. The color of the heat-treated molten mass in the test tube was compared with those of the standard color series to determine the corresponding color of heat-treated molten sample mass.

As will be seen from the results shown in Table 1, the product according to this invention is higher in yield, lower in content of free maleic acid which acts as an impurity, thus higher in content of maleic anhydride, and excellent in heat resistant property.

EXAMPLE 4

50 Grams of a colloidal silica (AEROSIL 200 produced by Nippon Aerosil Co., Ltd.) having a particle size of 12 microns was added to 10 kg of maleic anhydride of fine particle form sieved through a 10 mesh metal screen. The admixture was subjected to blending in a tumbler type mixer for 10 minutes under dry condition to obtain a maleic anhydride composition.

EXAMPLE 5

Similarly as in Example 4, 5 grams of a colloidal silica (AEROSIL 200 produced by Nippon Aerosil Co., Ltd.) having a particle size of 12 microns was added to 10 kg of maleic anhydride of fine particle form sieved through a 10 mesh metal screen. The admixture was subjected to blending in a tumbler type mixer for 10 minutes under dry condition to obtain a maleic anhydride composition.

EXAMPLE 6

Into a 20 liter polyethylene bag, charged were 10 kg of molten maleic anhydride maintained at 60° C. and 20 grams of a hydrophobic colloidal silica (TULLANOX 500 produced by Tulco Inc., U.S.A. and sold by Gunze Sangyo Inc.). The bag was closed by heat sealing, and one side edge of the bag was swingably pivoted and the opposed side edge of the bag was connected to a rotary motor fitted with a reduction gear to be moved in the vertical direction at a rate of 20 times per minute. The content in the container was cooled spontaneously for 5 hours until it reached the room temperature while being moved continuously, whereupon fine crystal particles were separated. The thus formed crystal particles were sieved through a 10 mesh metal screen to obtain 9.8 kg of a maleic anhydride composition having a particle size of passing through a 10 mesh screen and containing the colloidal silica.

EXAMPLE 7

Generally following the procedures as described in Example 6 except that 200 grams of a hydrophobic colloidal silica (AEROSIL R-972 produced by Nippon Aerosil Co., Ltd.) was added to 10 kg of molten maleic anhydride maintained at 60° C., whereby 9.9 kg of a maleic anhydride composition of fine particle form was prepared.

COMPARATIVE EXAMPLE 4 to 7

Following the procedures as described in Example 4, conventional lubricants for powder products were used as the caking prevention materials to prepare four comparative maleic anhydride compositions as set forth below.

Comparative Example 4: No caking prevention material was added.
Comparative Example 5: 100 grams of calcium stearate was added.
Comparative Example 6: 300 grams a polyethylene wax (SAN WAX 171 P produced by Sanyo Chemical Industries, Inc.) was added.
Comparative Example 7: 300 grams of a polyethylene powder (MICROU-M produced by Chubu Microchemical Co. Ltd.) was added.

The fluidity of each of the compositions of Examples 4 to 7 and Comparative Examples 4 to 7 was determined by the following fluidity test. 500 grams for each of the compositions was put into a 1 liter glass bottle and stored stationarily at room temperature for three months. After the lapse of three-month storage period, the glass bottle was tilted to examine whether the content therein was maintained in the fluidal condition or not and to check whether the powder in the glass bottle had caked or not. The results are shown in Table 2.

TABLE 2

| Content of Added Material | (part)* | Fluidity |
|---|---|---|
| Example 4 | 0.5 | Good |
| Example 5 | 0.05 | Good |
| Example 6 | 0.2 | Good |
| Example 7 | 2 | Good |
| Comparative Example 4 | 0 (none) | Not flowed |
| Comparative Example 5 | 1 | Not flowed, but became flidized by vigrous shaking |
| Comparative Example 6 | 3 | Not flowed, but became flidized by vigrous shaking |
| Comparative Example 7 | 3 | Solidified and not flowed |

*Note: "Part" means part by weight of each caking prevention material added to 100 parts by weight of maleic anhydride.

As will be readily seen from the results set forth in Table 2, the compositions prepared in accordance with this invention are excellent in fluidity so that no caking has occurred during the storage time although the amounts of colloidal silica added thereto are so small as of not more than 1 part by weight.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A method of preparing fine crystal particles of maleic anhydride, which comprises the steps of putting a molten mass of purified maleic anhydride into a hermetically closed container moved at a moving rate of 1 to 30 times per minute, and slowly cooling said molten mass of maleic anhydride to room temperature over a period of not less than 3 hours while keeping under the moving condition separated fine crystals of maleic anhydride having a particle size which passes through a sieve of 10 mesh.

2. The method as recited in claim 1, wherein said molten mass of maleic anhydride is prepared by heating to melt maleic anhydride at a temperature of from 55° to 100° C.

3. The method as recited in claim 1, wherein said molten mass of maleic anhydride is a molten product obtained through a process for preparing maleic anhydride.

4. The method as recited in claim 1, wherein said hermetically closed container is rotated to keep said separated fine crystals of maleic anhydride under the moving condition.

5. The method as recited in claim 1, wherein said hermetically closed container is inverted to keep said fine separated crystals of maleic anhydride under the moving condition.

6. The method as recited in claim 1, wherein one side edge of said hermetically closed container is pivoted and the opposed side edge is moved periodically in the vertical direction to keep said separated fine crystals of maleic anhydride under the moving condition.

* * * * *